(12) United States Patent
McBurney et al.

(10) Patent No.: US 6,508,983 B1
(45) Date of Patent: Jan. 21, 2003

(54) EXCHANGER APPARATUS AND METHOD OF MANUFACTURE

(75) Inventors: Laura L. McBurney, Arvada, CO (US); Tom L. Clark, Windsor, CO (US); Randy E. Livingston, Aurora, CO (US)

(73) Assignee: COBE Cardiovascular, Arvada, CO (US)

( * ) Notice: Subject to any disclaimer, the term of this patent is extended or adjusted under 35 U.S.C. 154(b) by 0 days.

(21) Appl. No.: 09/356,762

(22) Filed: Jul. 19, 1999

(51) Int. Cl.⁷ .......................... A61M 1/14; A61M 1/34; A61M 37/00; B01D 53/22
(52) U.S. Cl. .......................... 422/44; 422/48; 604/6.14; 604/4.01; 96/10
(58) Field of Search ...................... 422/44–48; 604/4.01, 604/6.09, 6.13, 6.14; 210/321.6, 321.61, 321.72, 321.75, 321.78–321.79, 500.1–500.21, 500.23, 322, 323.1, 348, 416.1, 487, 650; 128/DIG. 3; 165/58, 60, 75, 100–103, DIG. 355; 261/2–3, 158–161, 19–22, 75, DIG. 28; 96/4, 7–11, 243, 267

(56) References Cited

U.S. PATENT DOCUMENTS

| | | | |
|---|---|---|---|
| 3,536,611 A | 10/1970 | de Filippi et al. ............ 210/22 |
| 3,794,468 A | 2/1974 | Leonard .................... 23/258.5 |
| 4,227,295 A | 10/1980 | Bodnar et al. ............. 29/527.3 |
| 4,280,981 A | 7/1981 | Harnsberger ................. 422/46 |
| 4,336,224 A | 6/1982 | Siposs ........................ 422/46 |
| 4,376,095 A | 3/1983 | Hasegawa .................... 422/46 |
| 4,389,363 A | 6/1983 | Molthop .................... 264/135 |
| RE31,389 E | 9/1983 | Brauer et al. ............ 210/321.3 |
| 4,622,206 A | 11/1986 | Torgeson .................... 422/48 |
| 4,637,917 A | 1/1987 | Reed et al. .................. 422/46 |
| 4,645,645 A | 2/1987 | Martinez et al. .............. 422/46 |
| 4,657,743 A | 4/1987 | Kanno ........................ 422/46 |
| 4,659,549 A | 4/1987 | Hamada et al. ............... 422/48 |
| 4,698,207 A | 10/1987 | Bringham et al. ............. 422/46 |
| 4,715,953 A | 12/1987 | Leonard .................. 210/321.8 |
| 4,735,775 A | 4/1988 | Leonar et al. ................ 422/46 |
| 4,791,054 A | 12/1988 | Hamada et al. ................ 435/2 |
| 4,808,378 A | 2/1989 | Nakanishi et al. ............ 422/48 |
| 4,923,679 A | 5/1990 | Fukasawa et al. ............ 422/48 |
| 4,940,617 A | 7/1990 | Baurmeister ............... 428/36.3 |
| 4,975,247 A | 12/1990 | Badolato et al. ............. 422/48 |
| 5,045,446 A | 9/1991 | Goodrich, Jr, et al. .......... 435/2 |
| 5,120,501 A | 6/1992 | Mathewson et al. .......... 422/46 |
| 5,120,502 A | 6/1992 | Gordon et al. ................ 422/48 |
| 5,137,531 A | 8/1992 | Lee et al. .................... 422/46 |
| 5,143,312 A | 9/1992 | Baurmeister | |

(List continued on next page.)

FOREIGN PATENT DOCUMENTS

| | | |
|---|---|---|
| EP | 0 167 162 A2 | 1/1986 |
| EP | 0 380 307 A2 | 8/1990 |
| WO | WO 86/02914 | 5/1986 |

*Primary Examiner*—Angela D. Sykes
*Assistant Examiner*—P M Bianco
(74) *Attorney, Agent, or Firm*—Popovich & Wiles, PA

(57) ABSTRACT

An exchanger and method for manufacturing the same are disclosed. In one embodiment, the exchanger crimps a hollow fiber bundle along a length of a cylindrical case in at least two radial positions. At least one crimp is between an inlet port and an outlet port of a blood conduit. Preferably, the cylindrical case has two portions with different radii so that when the two portions are mated to enclose the hollow fiber bundle, crimping is achieved. In this way, shunting of blood is avoided by being forced to pass a crimped position between the inlet and outlet ports to more evenly distribute the blood among the fibers of the bundle. In another embodiment, a method for making an exchanger includes filling a chamber, integral to the exchanger, with uncured potting material. The exchanger is spun to distribute the uncured potting material about open ends of an encasement. After curing, a portion of the potting material and the hollow fiber bundle are trimmed away. Preferably, the cured potting material includes an annular relief.

19 Claims, 11 Drawing Sheets

U.S. PATENT DOCUMENTS

| | | | |
|---|---|---|---|
| 5,152,964 A | 10/1992 | Leonard | 422/48 |
| 5,162,101 A | 11/1992 | Cosentino et al. | 422/46 |
| 5,234,663 A | 8/1993 | Jones et al. | 422/46 |
| 5,236,665 A | 8/1993 | Mathewson et al. | 422/46 |
| 5,240,677 A | 8/1993 | Jones et al. | 422/46 |
| 5,242,995 A | 9/1993 | Kim et al. | 525/453 |
| 5,244,930 A | 9/1993 | Trudell et al. | 521/99 |
| 5,255,734 A | 10/1993 | Leonard et al. | 165/96 |
| 5,270,004 A | 12/1993 | Cosentino et al. | 422/46 |
| 5,316,724 A | 5/1994 | Mathewson et al. | 422/48 |
| 5,346,621 A | 9/1994 | Haworth et al. | 210/645 |
| 5,358,689 A | 10/1994 | Jones et al. | 422/46 |
| 5,376,334 A | 12/1994 | Haworth et al. | 422/46 |
| 5,382,407 A | 1/1995 | Leonard | 422/48 |
| 5,395,468 A | 3/1995 | Juliar et al. | 156/169 |
| 5,425,951 A | 6/1995 | Goorich, Jr. et al. | 424/520 |
| 5,429,184 A | 7/1995 | Bach et al. | 165/149 |
| 5,489,413 A | 2/1996 | Carson et al. | 422/46 |
| 5,514,335 A | 5/1996 | Leonard et al. | 422/46 |
| 5,580,522 A | 12/1996 | Leonard et al. | 422/46 |
| 5,618,887 A | 4/1997 | Bamford et al. | 525/279 |
| 5,626,819 A | 5/1997 | Novello et al. | 422/45 |
| 5,718,869 A | 2/1998 | Bach et al. | 422/45 |
| 5,718,871 A | 2/1998 | Elgas | 422/46 |
| 5,728,420 A | 3/1998 | Keogh | 427/2.12 |
| 5,747,138 A | 5/1998 | Leonard | 428/113 |
| 5,753,173 A | 5/1998 | Leonard et al. | 264/503 |
| 5,762,868 A | 6/1998 | Leonard | 422/46 |
| 5,762,875 A | 6/1998 | Gremel et al. | 422/45 |
| 5,817,278 A | 10/1998 | Fini et al. | |
| 5,823,987 A | 10/1998 | Elgas et al. | 604/4 |
| 6,113,782 A * | 9/2000 | Leonard | 210/321.61 |
| 6,258,321 B1 * | 7/2001 | Van Driel et al. | 210/500.23 |

\* cited by examiner

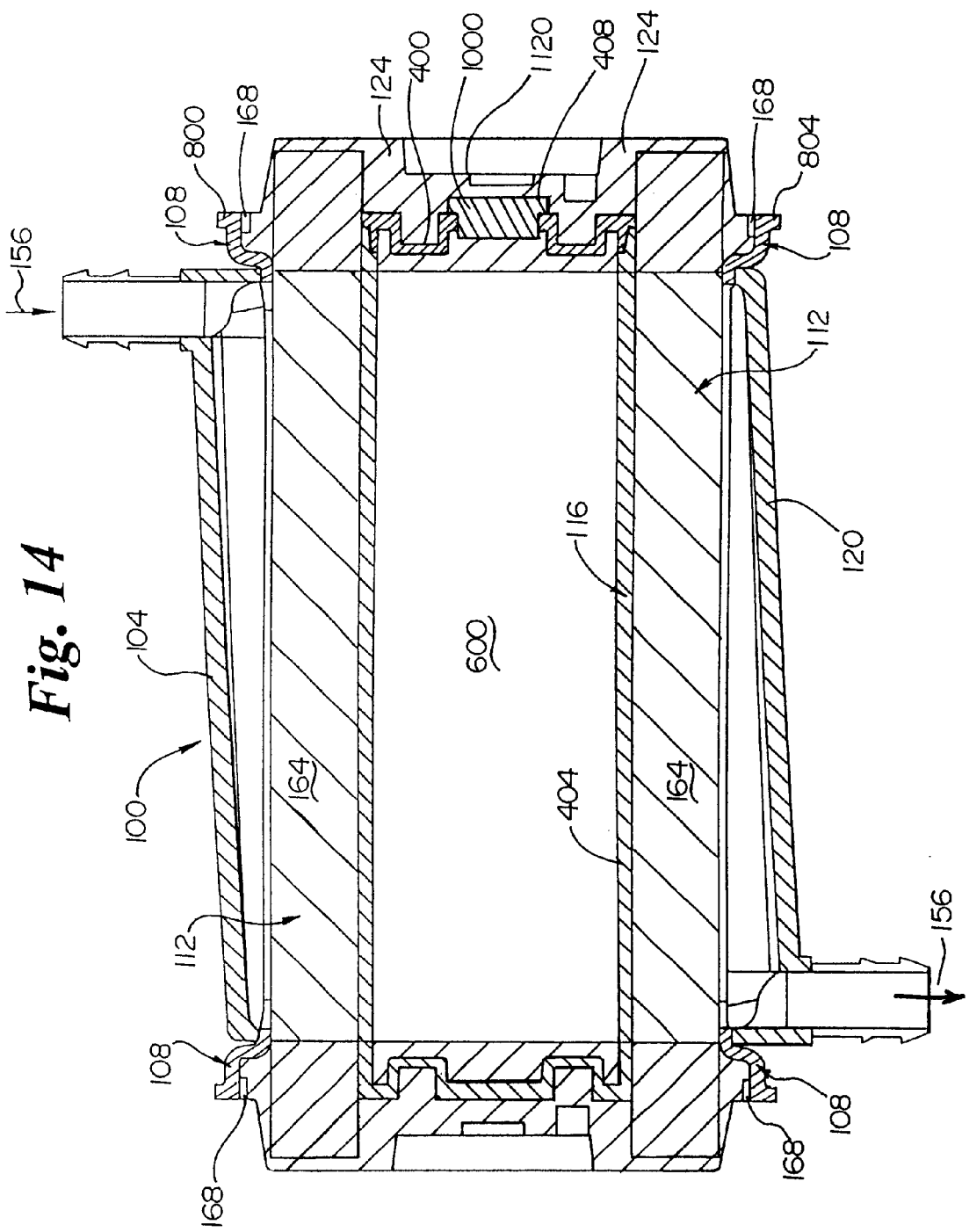

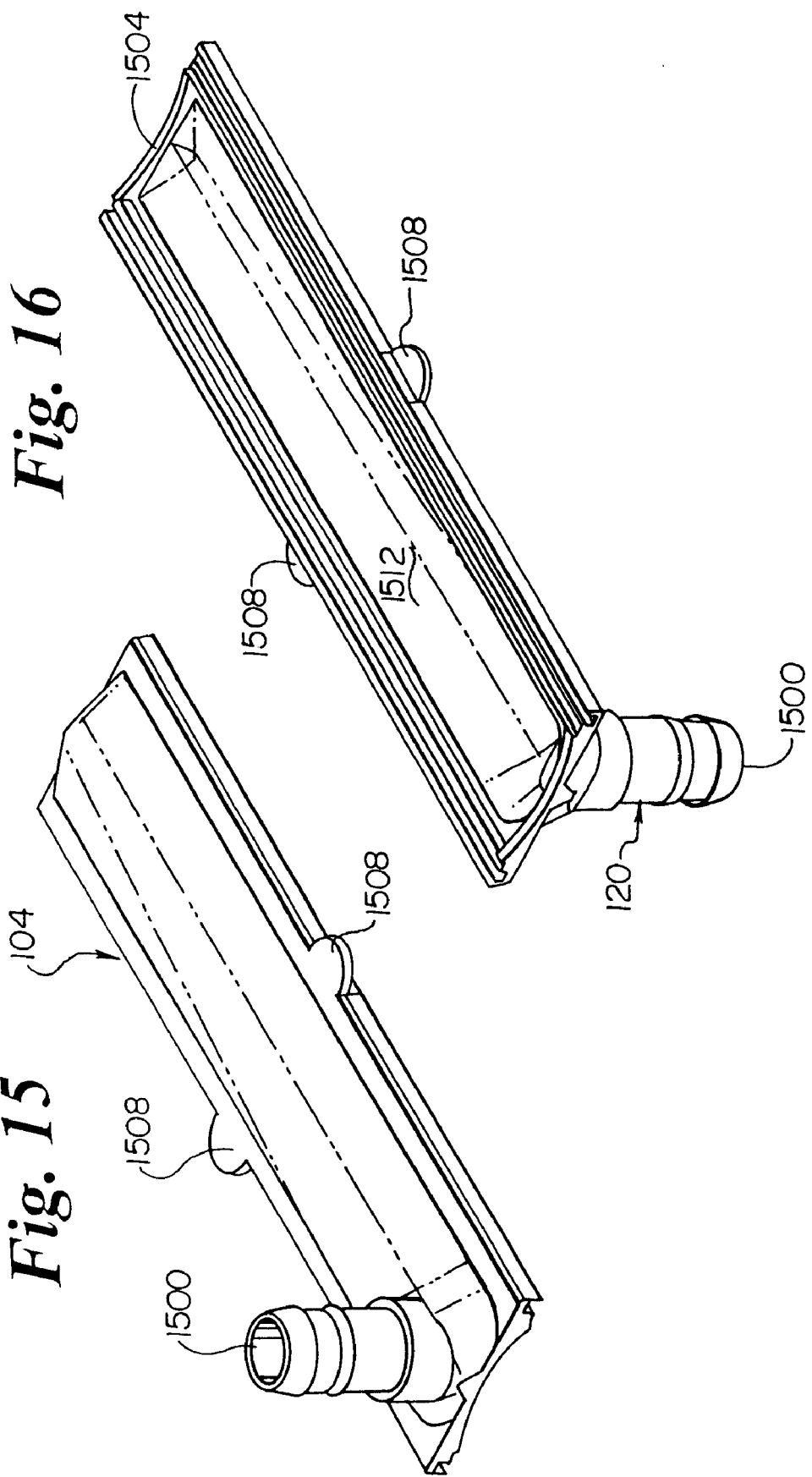

EXCHANGER APPARATUS AND METHOD OF MANUFACTURE

FIELD OF THE INVENTION

The present invention relates generally to a membrane exchanger and more particularly to a hollow fiber exchanger which avoids shunting and is easy to manufacture.

BACKGROUND OF THE INVENTION

During certain surgeries, natural cardiovascular activity is suspended. Accordingly, the bloodstream requires extracorporeal oxygenation in lieu of the lungs. Exchangers perform this oxygenation of the blood through use of one or more membranes which each allow gasses to pass freely, but resist liquids from passing across each membrane. In this way, oxygen is added to and carbon dioxide is removed from the bloodstream.

Exchangers come in many shapes and forms, but generally, there is a liquid or a blood conduit and a gas or an air conduit. In membrane exchangers, the liquid does not typically contact the gases directly. The air and blood conduits are divided by membranes in an exchange chamber. At an inlet end, the air conduit is divided to flow within a number of hollow fiber membranes. At the inlet end of the hollow fibers, the air is rich in oxygen, however, at an outlet end, the air is oxygen depleted and carbon dioxide rich. The blood conduit starts at an inlet port, travels outside of the hollow fiber membranes within the exchange chamber and exits an outlet port. Potting around the ends of the hollow fiber membranes keeps the blood from escaping the exchanger or directly mixing with the air.

To avoid shunting, the hollow fibers should be tightly packed within the exchange chamber. The term "shunting" describes an undesired process whereby the blood avoids contact with the hollow fibers such that oxygenation is stifled. For example, when the hollow fibers are not tightly packed against the walls of the chamber, blood can flow within the resulting gap while passing from the inlet port to the outlet port, therefore bypassing the fibers.

Conventional exchangers attempt to solve the shunting problem in a variety of ways. In one example, the size of the fiber bundle is tightly controlled so that when the bundle is inserted into an enclosure, the fibers are tightly packed against the wall. The insertion involves sliding the fiber bundle into the enclosure. Unfortunately, tight control of the fiber bundle size is difficult such that shunting occurs if the bundle is too small. On the other hand, if the bundle is too large, the bundle will not slide into the enclosure easily and can result in damaging the fibers. These problems have plagued prior attempts to manufacture exchangers which solve the shunting problem. Further, these exchangers are generally difficult and/or expensive to manufacture.

Potting material is used during manufacture of the exchanger to seal the inlet and outlet ends of the hollow fibers from the blood within the exchange chamber. Typically, during manufacture an external reservoir is connected to the exchanger. A tube connected to the reservoir allows fluid communication with an area near the ends of the hollow tubes. Either gravity or centrifugal force is used to cause uncured potting material to flow and hold it in place while curing. Unfortunately, the potting reservoir and tube generally becomes fouled with potting material after a few uses and must be replaced. Additionally, when subjected to the centrifugal force, the tube can come loose which results in potting material being sprayed out of the reservoir.

Methods using centrifugal force generally pot one end of the exchanger at a time. The exchanger is first spun about a first end to create centrifugal force which disburses the potting material from the potting reservoir to a second end of the exchanger. After curing the second end, the exchanger is spun about the second end to disburse potting material from another potting reservoir to a first end of the exchanger. In this way, both ends of the exchanger are successively potted.

After curing, any excess potting material is trimmed away. During trimming a portion of the hollow tube ends are typically removed along with the excess potting material. A sharp tool is used to slice away the unwanted portion of potting material. Unfortunately, the potting material can delaminate from the wall of the exchange chamber during the trimming process. When the sharp tool is used to trim, the blade temporarily compresses the potting material such that it may peel away from the wall. Even though the potting material may resume its uncompressed shape after delamination, during use, the blood and air can pass along the wall and around the potting material. As can be appreciated, delamination ruins the exchanger.

A need, therefore, exists for an exchanger design which avoids shunting without being difficult to manufacture. During manufacture, such an exchanger should eliminate the need for external potting reservoirs. Moreover, such an exchanger should not be susceptible to delamination during the trimming process.

SUMMARY OF THE INVENTION

In accordance with the present invention, an exchanger and method for manufacturing the same are disclosed. In one embodiment, the exchanger has a cylindrical case which crimps a hollow fiber bundle along a length of the cylindrical case in at least two radial positions. At least one crimp is between an inlet port and an outlet port of a blood conduit. Preferably, the cylindrical case has two portions with different radii so that when the two portions are mated to enclose the hollow fiber bundle, crimping is achieved. In this way, shunting of blood is avoided by being forced to pass a crimped position between the inlet and outlet ports to more evenly distribute the blood among the fibers of the bundle.

In another embodiment, a method for making an exchanger includes filling a chamber, integral to the exchanger, with uncured potting material. The exchanger is spun to distribute the uncured potting material through dispensing holes in the chamber ends and about both open ends of an encasement. After curing, a portion of the potting material and the hollow fiber bundle are trimmed away. Preferably, the cured potting material is molded such that the trimming is on a surface of the potting material away from an annular relief to help avoid delamination.

Based upon the foregoing summary, a number of important advantages of the present invention are readily discerned. Crimping the hollow fiber bundle in the blood conduit avoids shunting. Further, a potting reservoir integral to the exchanger avoids the problems associated with external potting reservoirs. Further still, delamination during trimming is avoided by the addition of the annular relief.

BRIEF DESCRIPTION OF THE DRAWINGS

FIG. 14 is a side-sectional view of the exchanger after potting, but before trimming;

FIG. 15 is a perspective view of a manifold;

FIG. 16 is another perspective view of the manifold of FIG. 15; and

DESCRIPTION OF THE PREFERRED EMBODIMENT

The present invention includes an exchanger and a method for manufacturing the same. This invention solves the problems with shunting, potting reservoirs and delamination present in the prior art. By doing so, the present exchanger is more efficient and easier to manufacture.

Figure 1:
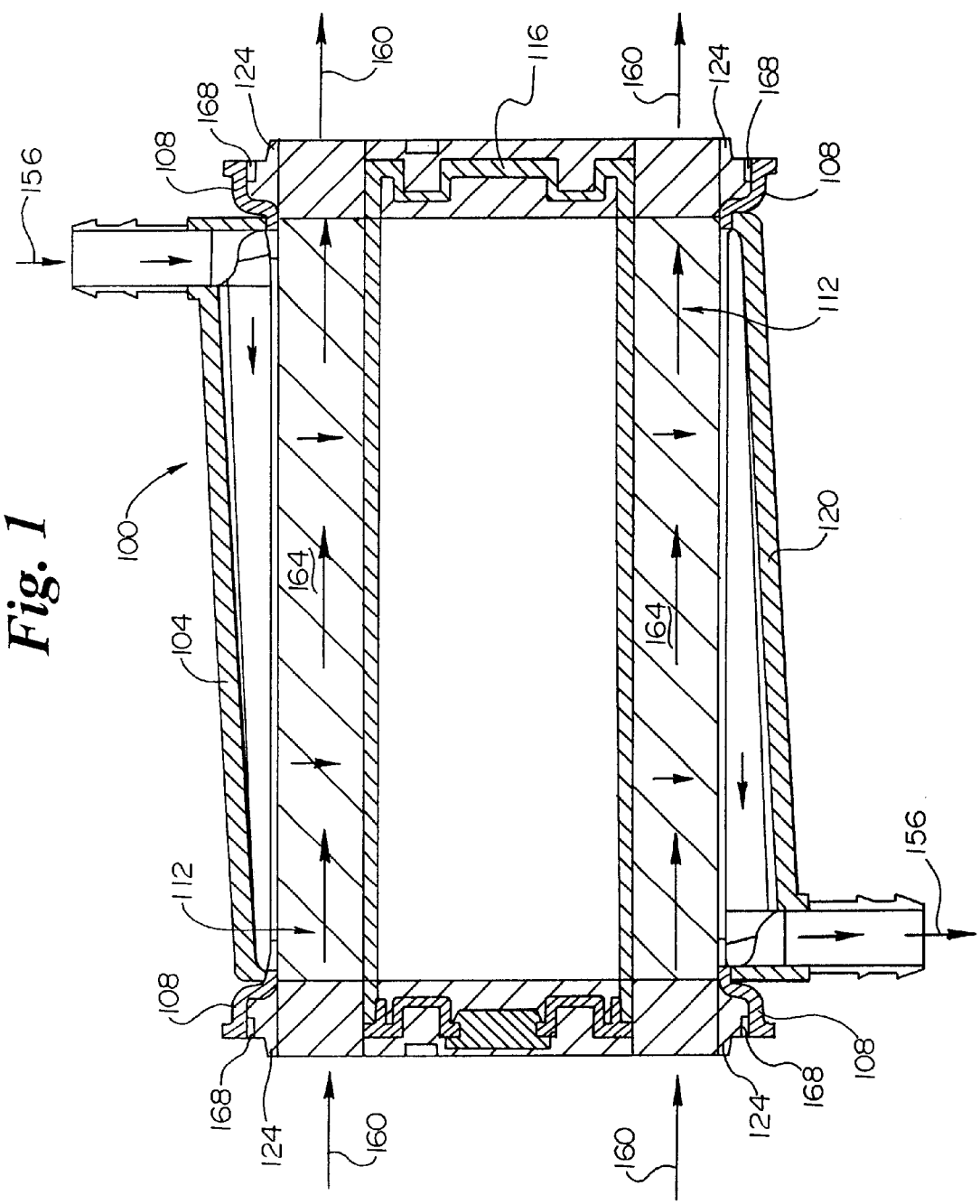
FIG. 1 is a schematic representation of a side-sectional view of one embodiment of an exchanger.
Figure 2:
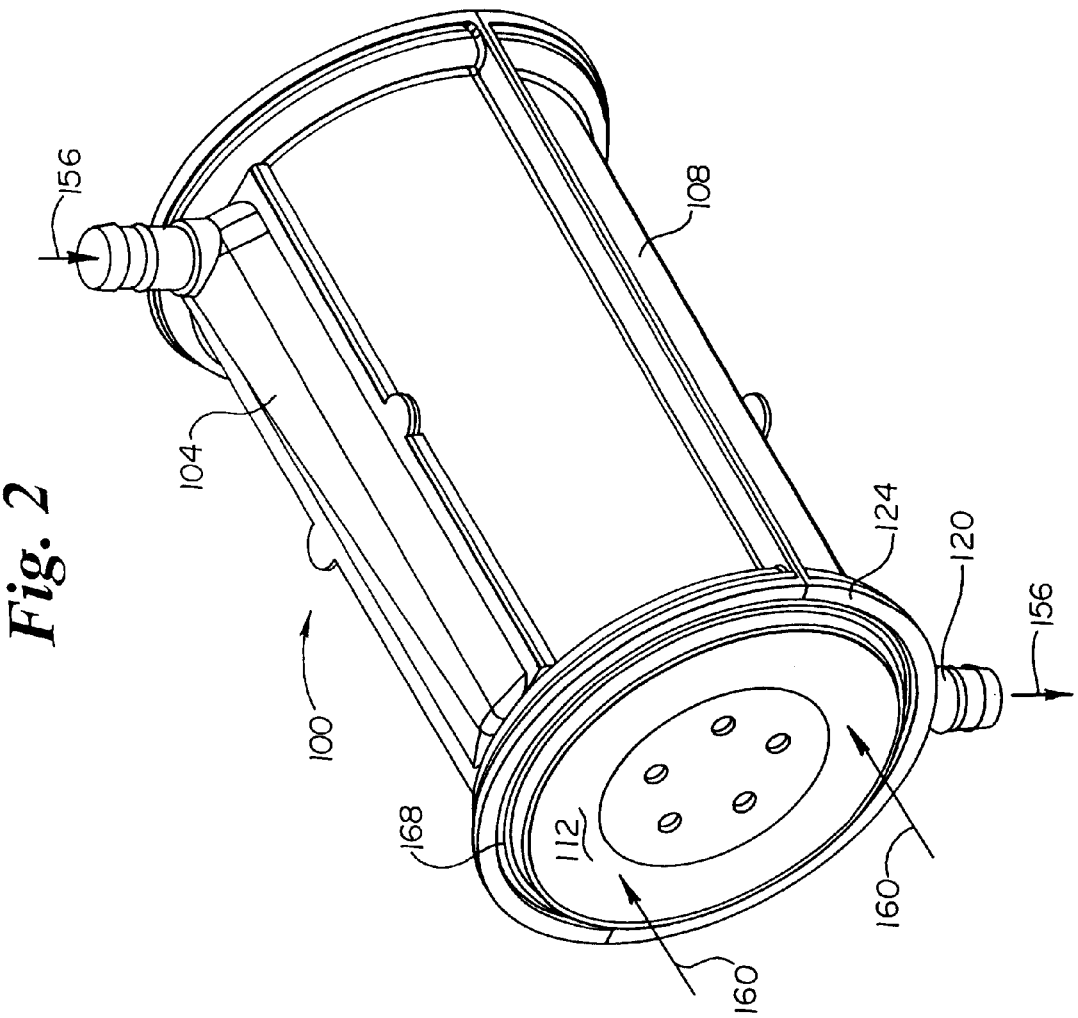
FIG. 2 is a perspective view of the exchanger without gas caps.
Figure 3:
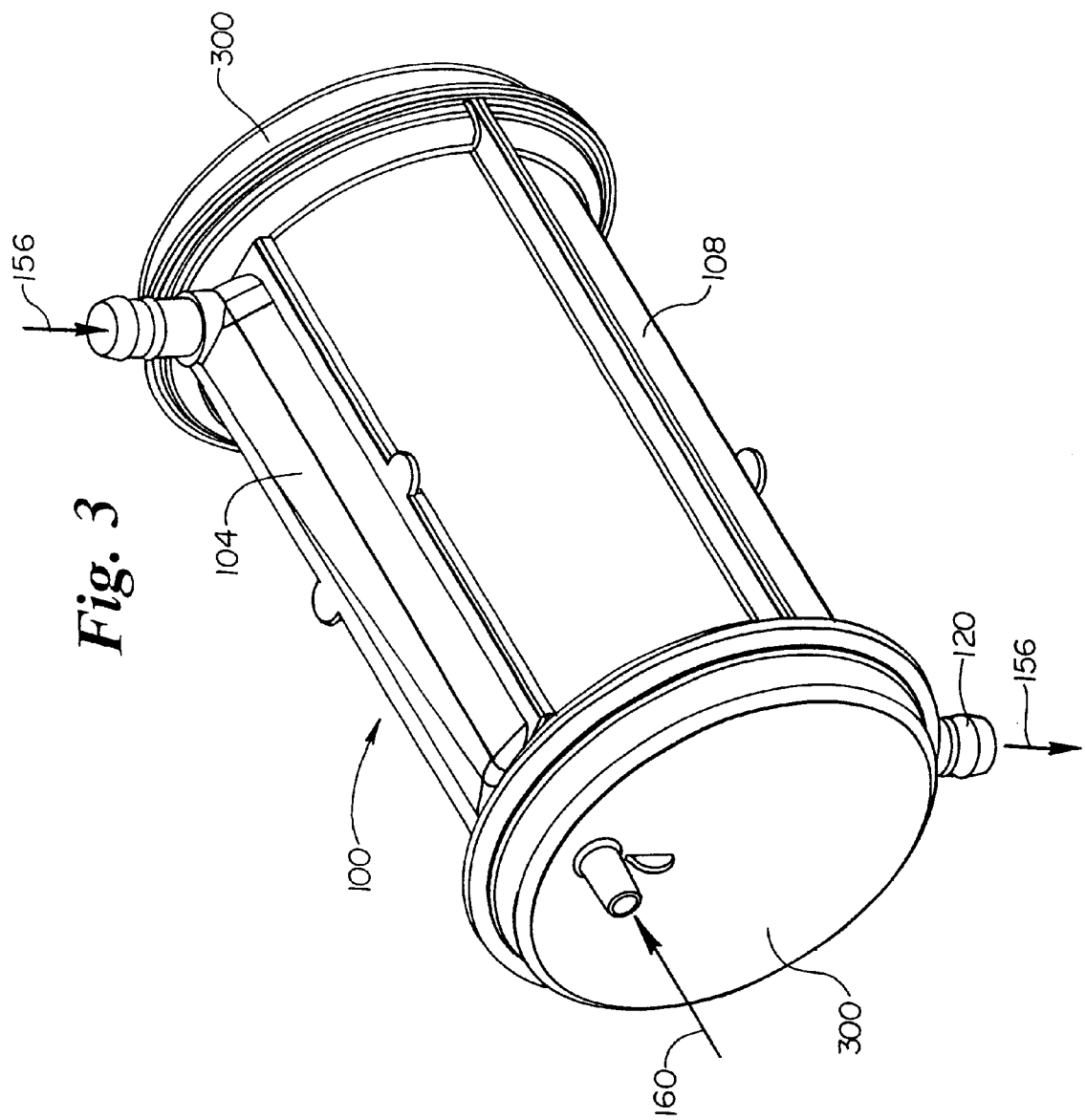
FIG. 3 is a perspective view of the exchanger with gas caps.

With reference to FIGS. 1–3, a side-sectional and two perspective views of an embodiment of the exchanger 100 are depicted. This embodiment of an exchanger 100 is used to oxygenate blood. Although not shown, a heat exchanger is often used in conjunction with the oxygenation process to heat the blood. Included in the exchanger 100 is an inlet manifold 104, a cylindrical case 108, a bundle of hollow fiber membranes 112, a hollow core 116, an outlet manifold 120, potting material 124, and gas caps 300. The potting material 124 has an annular relief 168 which helps avoid delamination. For ease of depiction, the potting material 124 on each end of the exchanger is shown having a profile with a flat surface which faces the center of the exchanger, however, it is to be understood that the surface has an annular shape which results from the centrifugal force used during curing. To encourage oxygenation of the blood, the inlet and outlet manifolds 104, 120 are coextensive with substantially a whole length of the cylindrical case 108. Air travels into the gas cap 300, inside each hollow fiber membrane and out another gas cap 300 so that blood on the outside of the fiber membranes is oxygenated. The process of oxygenation takes venous blood, adds oxygen and removes carbon dioxide to transform it into arterial blood.

Air and blood respectively travel through an air conduit and a blood conduit of the exchanger. The blood conduit is labeled with thick arrows 156 and is defined by the inlet manifold 104, an exchange chamber 164 and the outlet manifold 120. Venous blood enters the inlet manifold 104, is oxygenated in the exchange chamber 164 and is removed through the outlet manifold 120. The air conduit is marked with thin arrows 160 and divides the air into a number of individual streams which travel through individual fibers of the bundle 112 which at least extend a length of the cylindrical case or encasement is 108. Oxygen rich air enters the bundle of hollow fibers 112, provides oxygen to the blood in the exchange chamber 164, removes carbon dioxide from the blood, and exits the bundle of hollow fibers 112. The fibers in the bundle 112 are individual gas-permeable membranes which resist liquid from crossing the membranes but allow oxygen and carbon dioxide to pass freely. Potting material 124 surrounds ends of the bundle of fibers 112 and core 116 to keep the air from mixing directly with the blood and to hold the fibers in place.

Figure 4:
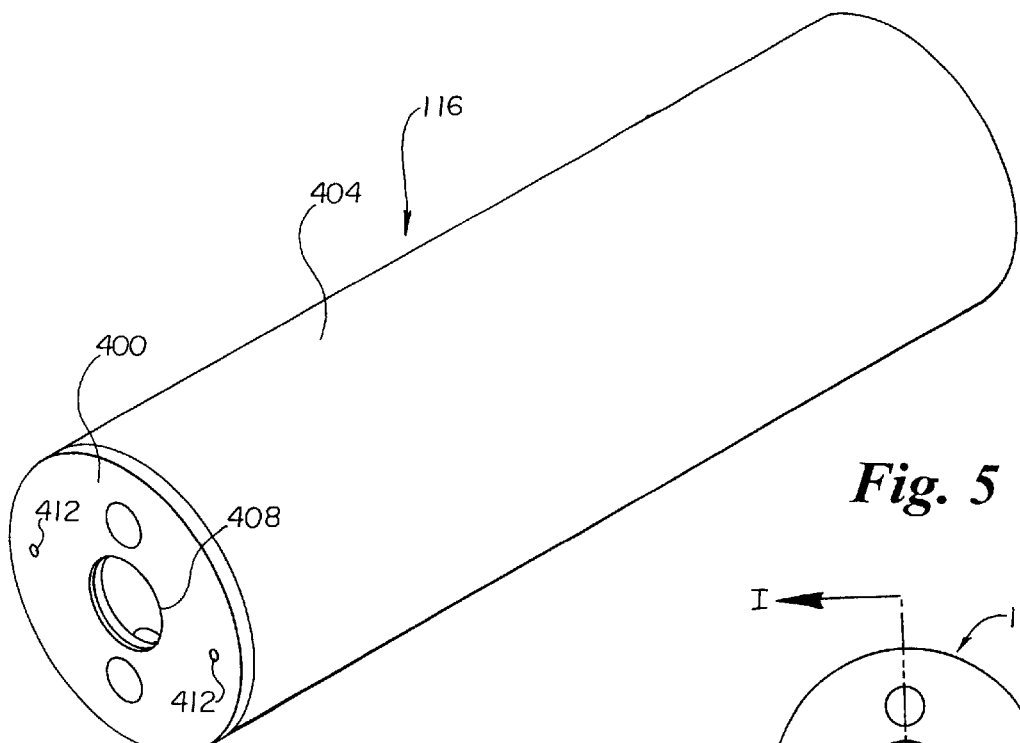
FIG. 4 is a perspective view of a core which is used as a potting reservoir.
Figure 5:
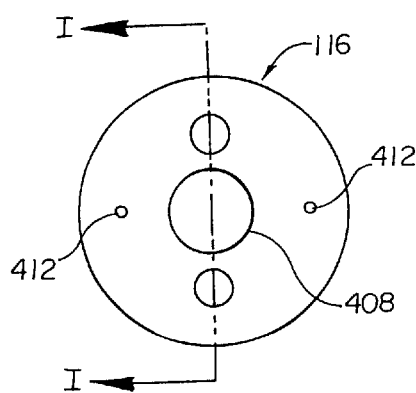
FIG. 5 is a top view of the core of FIG. 4.
Figure 6:
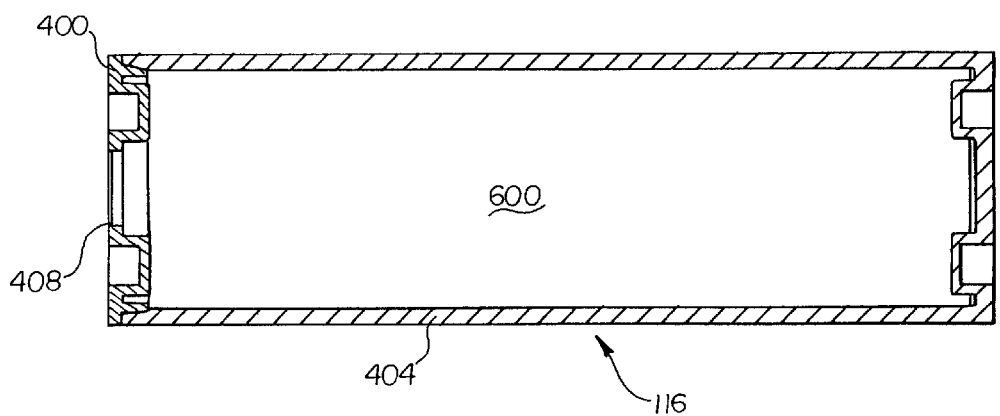
FIG. 6 is a side-sectional view of the core along a line I—I shown in FIG. 5.

With reference to FIGS. 4–6, the hollow core or core chamber 116 is respectively depicted in perspective, top and side-sectional views. The core 116 serves as a reservoir for uncured potting material during the manufacturing process. The core is an assembly comprised of a cylindrical portion 404 and a top portion 400. The cylindrical portion 404 has a generally closed bottom end and an open top end which forms a cup-like configuration. The top portion 400 is welded or glued to the open top end in order to create a substantially enclosed potting chamber 600. During the manufacturing process, uncured potting material is poured into a fill hole 408 in the top portion 400. A core plug 1000 (see FIG. 10) is placed over the fill hole 408 to keep the potting material from leaking out. Both the top portion 400 and the closed bottom end of the core 116 have two dispensing holes 412 which are oriented during assembly to generally lay in a same plane. Other embodiments could have more than two dispensing holes, for example, four dispensing holes on each end of the core. To help avoid leakage of the potting material during the fill process, the dispensing holes 412 are generally orientated in a horizontal plane, as shown in FIG. 4. Although potting material can leak during the fill process, leakage is restrained by the diameter of the dispensing holes 412 and the viscosity of the potting material. Further, a potting cap 1100 (see FIG. 11) serves to retain leakage, if there is any.

Figure 7:
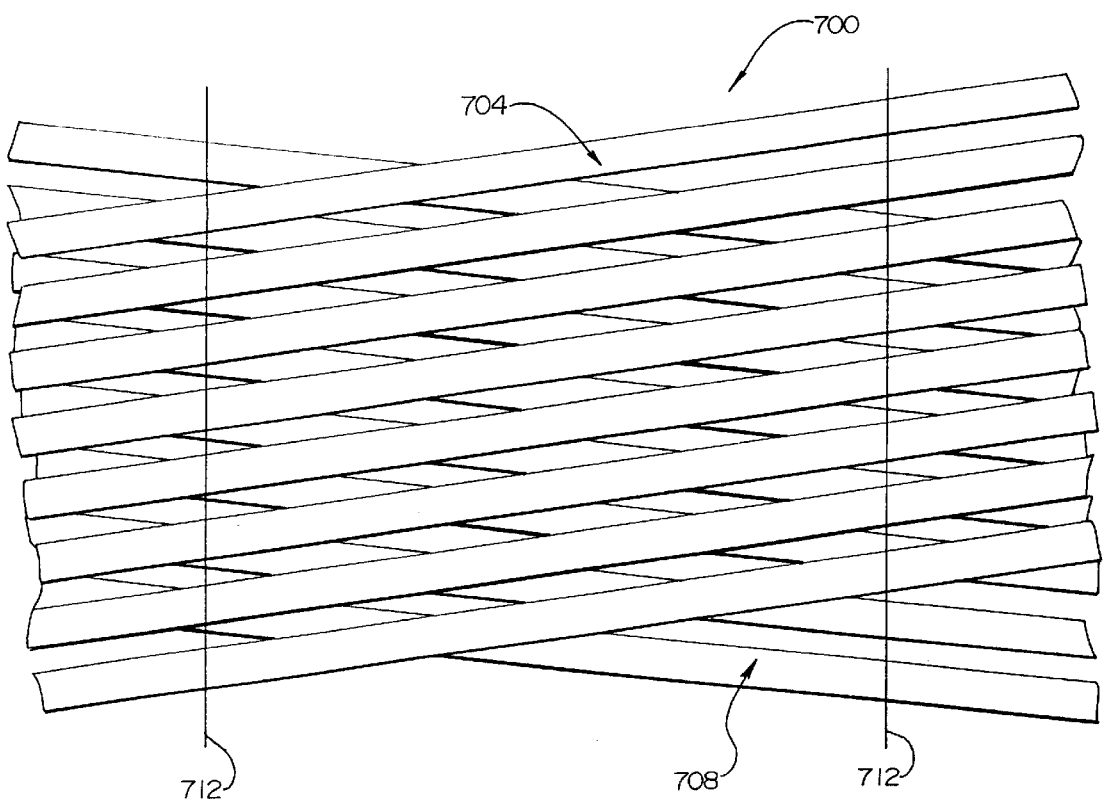
FIG. 7 is a side view of a portion of a mat of hollow fiber membranes which is wound around the core in one embodiment.

With reference to FIG. 7, a portion of a hollow fiber mat 700 is shown. The fiber mat 700 is comprised of a first layer of hollow fiber membranes 704 and a second layer of hollow fiber membranes 708. The hollow fibers are microporous and semi-permeable. Each layer of hollow fibers 704, 708 is arranged at an angle offset from the other layer 708, 704 to enhance gas transfer with the blood. The hollow fibers are preferably made of polypropylene, but could be any other material which generally allows gases to cross the membrane while resisting liquids to cross, such as polyethylene or polysulfone. Warp threads 712 are used to keep each layer 704, 708 properly orientated with respect to the other 708, 704. Preferably, the warp threads 712 are polyester, but could be any other material which maintains the orientation of hollow fibers 704, 708 such as polyethylene or polypropylene. The mat 700 is cut in a way to seal closed the ends of each hollow fiber 704, 708. Sealing avoids incursion of the potting material 124 into the hollow fibers 704, 708 during the potting process. The width of the mat 700 is longer than the length of the case 108, but not long enough to interfere with the potting caps 1100 (see FIG. 11). During manufacture of the exchanger 100, the sheet of fiber mat 700 is wound around the core 116 to form the fiber bundle 112. When the excess potting material is trimmed away, the sealed ends of the hollow fiber mat 700 are also trimmed away to provide unobstructed air conduits 160 through the exchange chamber 164.

Figure 10:
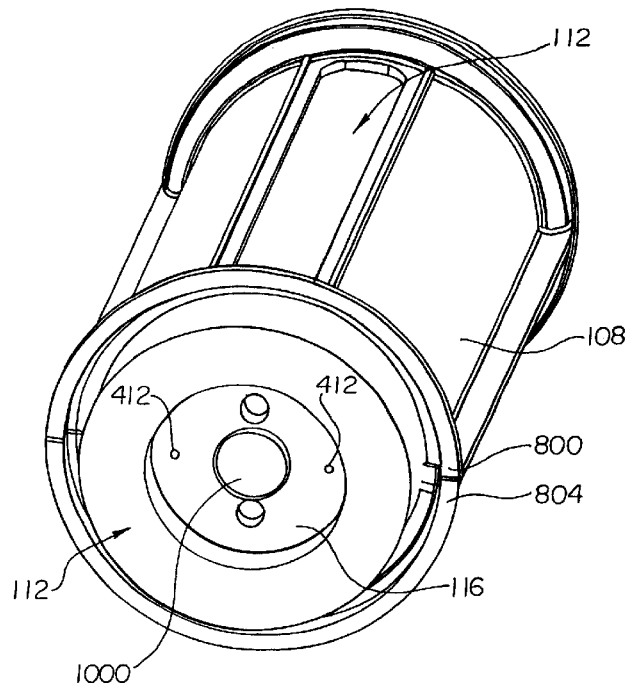
FIG. 10 is a perspective view of the case of FIG. 8 enclosing the core and a hollow fiber bundle.

Crimping of the bundle of hollow fibers 112 avoids shunting of the blood conduit 156. The hollow core 116 is cylindrically shaped and rigid. To form a core subassembly, the bundle of hollow fibers 112 are positioned around the core 116 in an annular ring. With reference to FIG. 10, the open-ended case 108 surrounds the core subassembly. As discussed in the background section, precisely controlling the diameter of the core subassembly is difficult. When the core subassembly is enclosed in the case 108, the exchange chamber 164 can experience loose packing of the bundle 112. This causes insufficient flow distribution or shunting.

Figure 8:
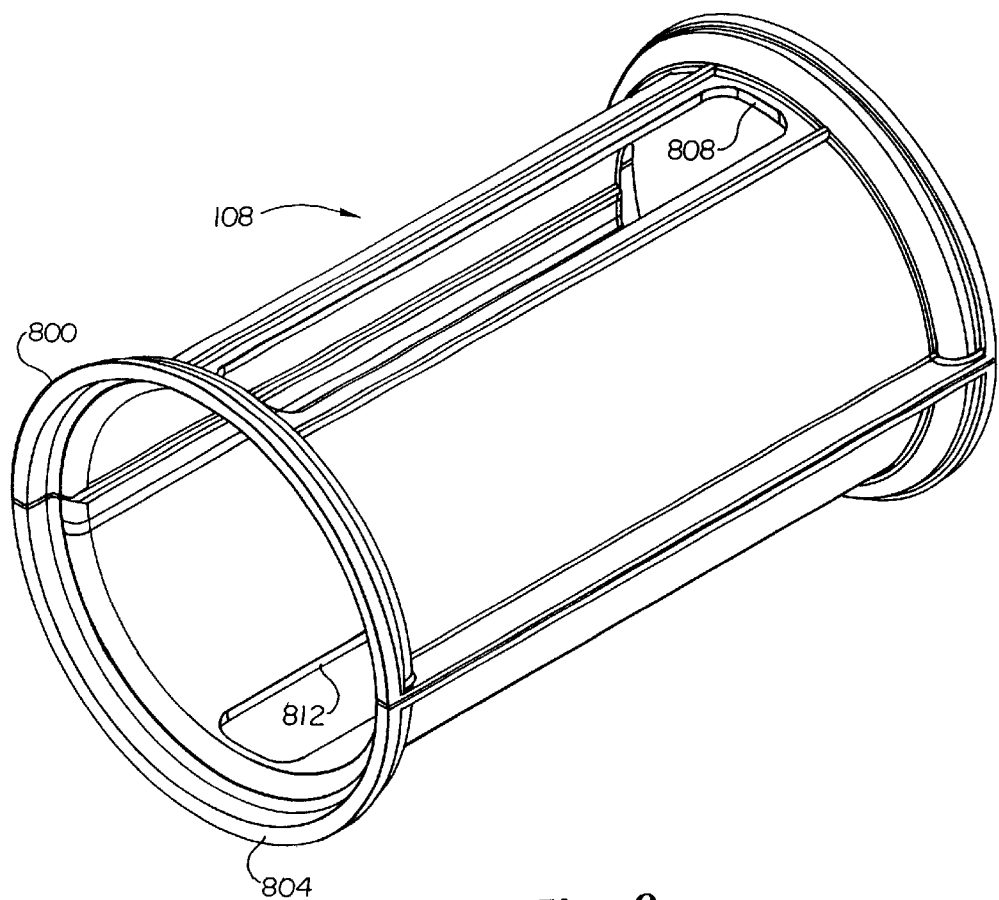
FIG. 8 is a perspective view of an open-ended cylindrical case without anything inside the case.
Figure 9:
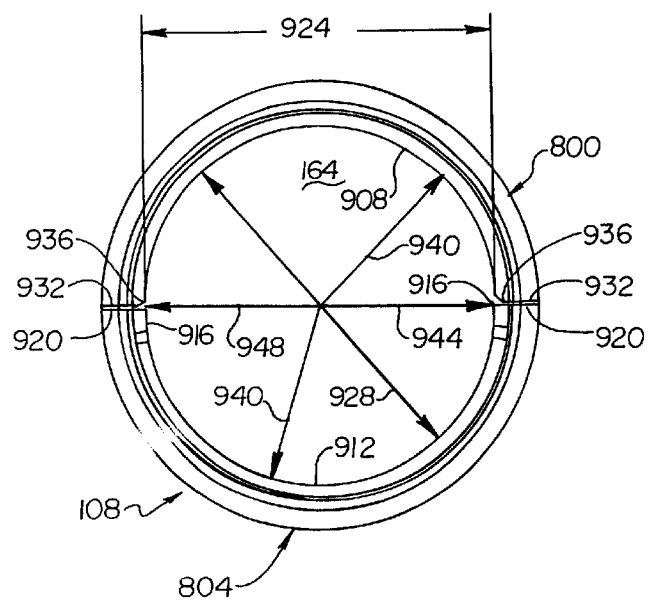
FIG. 9 is a top elevational view of the open-ended cylindrical case of FIG. 8.

Shunting is avoided in one embodiment by portions of the case 108 having different diameters which causes selective crimping of the rolled mat of hollow fibers 112. As shown in FIGS. 8–9, first and second partial cylinders 800, 804 form the cylindrical case 108. The first partial cylinder 800 has a first cut-out 808 and the second partial cylinder 804 has a second cut-out 812. Although not shown in these figures, the first cut-out 808 mates to the inlet manifold 104 and the second cut-out 812 mates to the outlet manifold 120. A first interior wall 908 of the first partial cylinder 800 is generally arcuately shaped, but, a second interior wall 912 of the second partial cylinder 804 deviates slightly from an arcuate shape in two regions 916 near edges 920 of the second partial cylinder 804. The two regions 916 result in the exchange chamber 164 having a first interior diameter 924 measured across the two regions 916 which is smaller than a second interior diameter 928 away from those regions 916. In one embodiment, the first interior diameter 924 is 2.840 inches (72.136 mm) and the second interior diameter 928 is 2.865 inches (72.771 mm) for a ratio of 99.13%. The fiber bundle diameter for this embodiment is generally about 2.9 inches ( 73.7 mm) so that the first interior diameter crimps the fiber bundle by about 2% or more. Testing has shown the preferred range of crimping is between 1.31 and 4.2%.

The crimping of the interior surface of the case 108 can be described in terms of radii rather than diameters. The first interior wall 908 has a first radius 940 and the second interior wall 912 has portions with the first radius 940, but also has portions with a second radius 944 near the two regions 916. Because the second radius 944 is less than the first radius 940, the fiber bundle 116 is crimped near the two regions 916. In one embodiment, the two regions 916 are substantially flat.

The differing diameters 924, 928 result in the case 108 crimping the annularly-shaped fiber bundle 112 at two radial positions along a length of the case. The exchange chamber 164 extends around the core 116 to define two major blood conduits 156 along either side of the core 116. When traveling between first cut-out 808 and the second cut-out 812, the blood can take either of the major blood conduits 156. To provide crimping of all the blood flow, each of the two major blood conduits is subjected to a crimp at one radial position along the length of the case 108. In the embodiment of FIG. 9, the radial position of the crimps are opposite each other and about midway between the first and second cut-outs 808, 812.

The shape of the first and second interior wall 908, 912 avoids pinching of the hollow fiber mat 700 between the first and second partial cylinders 800, 804. Near edges 932 of the first partial cylinder 800, the terminal portions 936 of the substantially arcuate shape of the first interior wall 908 flares outwardly so that an interior surface of the terminal portions are at a third radius 948 larger than the first and second radii 940, 944. When the first partial cylinder 800 is mated to the second partial cylinder 804, as can be appreciated by those skilled in the art, the outwardly flared terminal portions 936 of the first interior wall 908 tend to avoid pinching the fiber mat 700 during the mating of the partial cylinders 800, 804. To further avoid pinching, both sides of the core subassembly (i.e., the fiber mat 112 and core 116) near the narrowed 916 and edge regions 920, 932 may be wrapped in a sheet of polytetrafluoroethylene (PTFE) (commercially available under the trade designation TEFLON) or other similar material before placing it in the second partial cylinder 804. Gathering of the fiber mat 700 is undesirable because it makes welding of the partial cylinders 800, 804 difficult and may rupture some hollow fiber membranes 704, 708.

Referring to FIG. 10, a perspective view of the core 116, case 108 and fiber bundle 112 are shown before potting. At this point in the assembly process, the partial cylinders 800, 804 have been welded together to form the open cylinder shaped case 108. The welding can be performed, for example, by contacting the flat surfaces of the edges 920, 932 with a heated platen and then bringing them into contact with each other to hot-plate weld the edges 920, 932 together. It is noted, other known welding and gluing methods could alternatively be used. Before potting, the hollow fiber bundle 112 extends beyond the ends of the case 108. While in the orientation shown in FIG. 10, uncured potting material is added to the chamber 600 defined by the core 116. Care is taken to avoid adding too much potting material such that it flows out the dispensing holes 412 on each end of the core 116. After adding the potting material, a core plug 1000 is inserted into the fill hole 408 of the core 116 in order to help retain the potting material. The potting material is preferably a liquid compound which cures to form a plastically deformable solid material. Preferably, the potting material is one of many varieties of polyurethane. Additionally, epoxies, thermoset materials or liquid silicone could be used.

Figure 11:
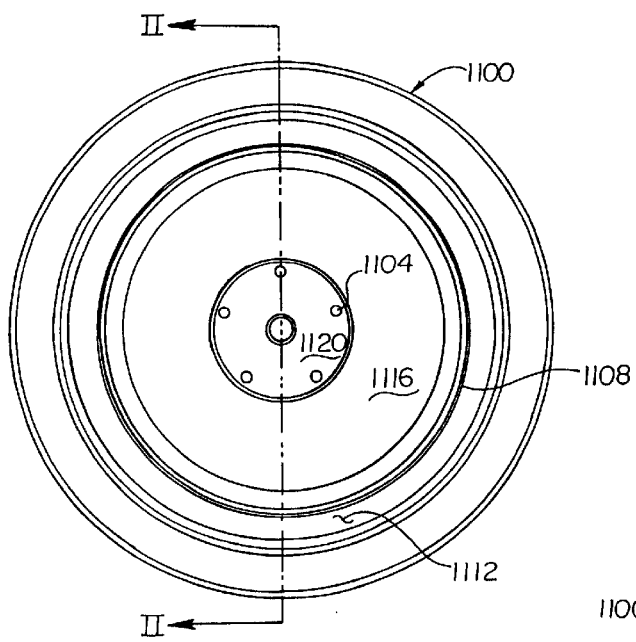
FIG. 11 is a bottom-elevational view of an embodiment of an end cap which seals the case during potting.
Figure 12:
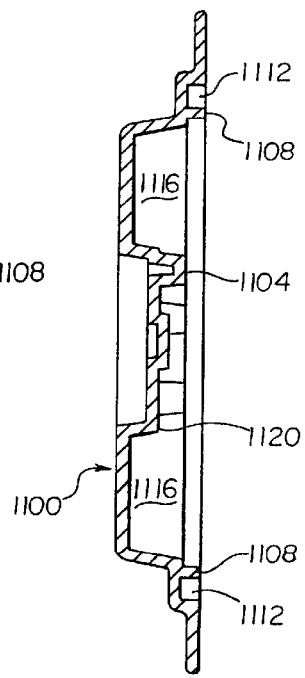
FIG. 12 is a side-sectional view of the end cap of FIG. 11.

With reference to FIGS. 11 and 12, bottom-elevational and side-sectional views of a potting cap 1100 are respectively illustrated. Two potting caps 1100 are used to cover the open ends of the case 108 so that uncured potting material may seal those ends during potting to form a substantially sealed enclosure. During the potting process, uncured potting material in the core 116 passes through dispensing holes 412 to pot end portions defined by the potting caps 1100 and the encasement 108. The potting cap 1100 has an annular channel 1112 which mates to the open end of the case 108. An annular recess 1116 in the cap 1100 mates with the hollow fiber bundle portion extending out the open end of the case 108 (see FIG. 10).

An annular-shaped protrusion 1108 in the cap extends toward the inner wall 908, 912 of the case 108 and molds the annular relief 168 in the potting material. The annular relief 168 laterally extends the potting material away from the rigid case 108 so that delamination is avoided during the trimming process. As can be appreciated, if the potting material had no annular relief 168 and the potting material were sliced flush with the case 108, the pressure of the knife could cause delamination between the potting material 124 and case 108. In other words, the annular relief 168 allows deforming the potting material without peeling the potting material away from the case 108.

A central portion 1120 of the cap 1100 is generally coincident with a plane in which the trimming away of the cured potting material will take place after curing. The central portion 1120 is punctuated by a number of protrusions 1104. These protrusions 1104 help center the core 116 and prevent it from shifting during the potting process. Additionally, the protrusions 1104 help distribute the flow of the potting material as it fills the potting cap 1100. As can be appreciated by those skilled in the art, the potting material 124 will form the conjugate of an interior surface of the potting cap 1100 after curing. In other words, the potting cap 1100 serves as a mold for the potting material.

Figure 13:
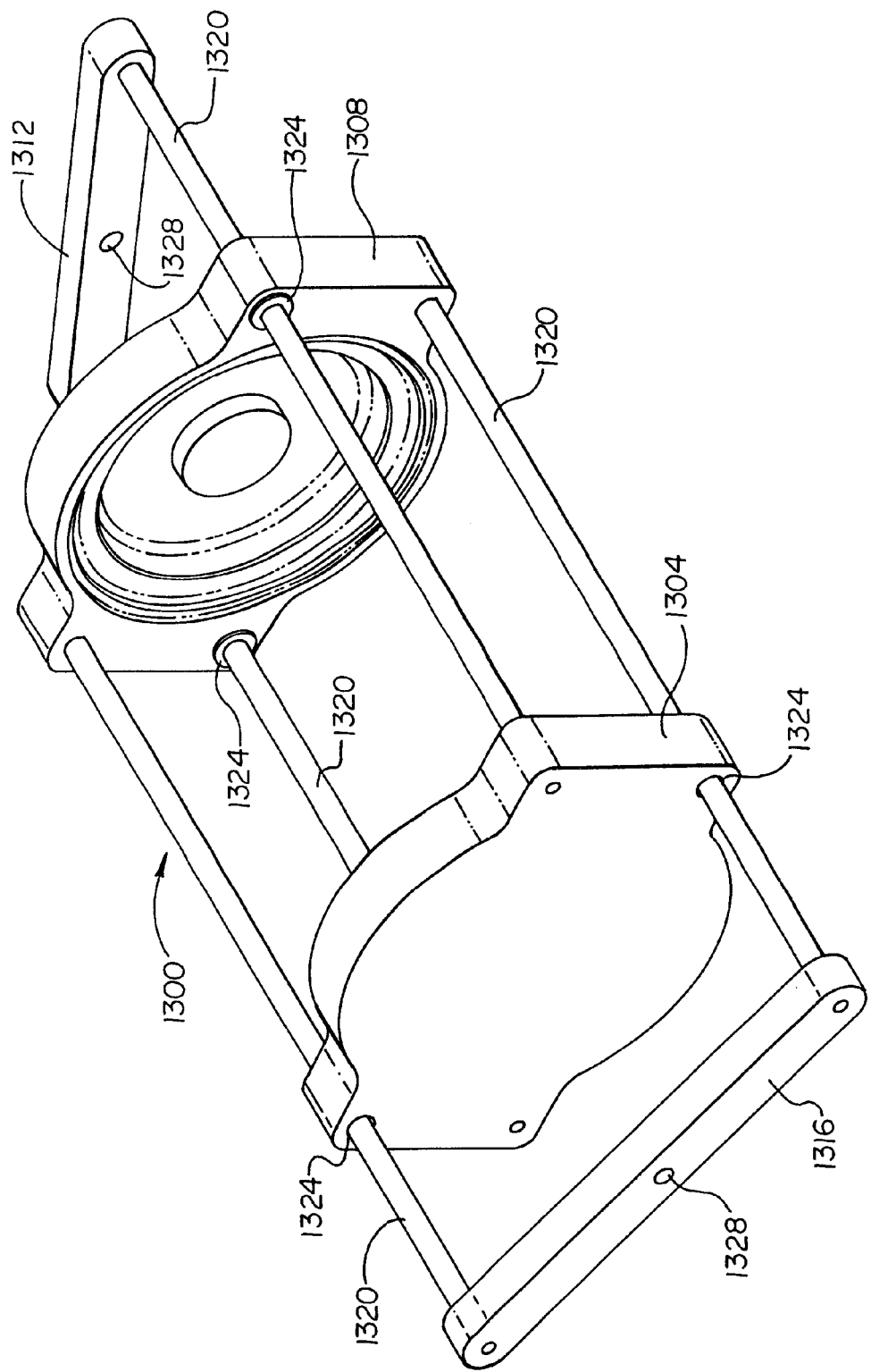
FIG. 13 is a perspective view of the potting jig which holds the end caps in place during potting.

With reference to FIG. 13, a perspective view of a potting jig 1300 is depicted. A first clamp 1304 and second clamp 1308 secure the potting caps 1100 to the case 108 during the potting process. A first counterweight 1312 and second counterweight 1316 are rigidly interconnected to their respective first and second clamps 1304, 1308 by rods 1320. The rods 1320 slide through guides 1324 so that the clamps 1304, 1308 can hold the potting caps 1100 in place during potting. The uncured potting material passes through the dispensing holes 412 of the core 116 when the exchanger 100 is spun about a central axis midway between the ends of the case 108. At the same time, the clamps 1304, 1308 use the centrifugal force generated by spinning to secure the potting caps 1100 during this process. To increase the centrifugal force at a given spin rate, additional counterweights can be attached to threaded holes 1328 in the first and second counterweights 1312, 1316.

Referring to FIG. 14, a side-sectional view of the exchanger 100 is shown after the potting process. The potting material 124 is generally molded into the conjugate of the potting cap 1100. After potting, the hollow fibers in the bundle 112 are typically enclosed within the potting material 124. However, since each fiber is sealed, the potting material is not within the hollow fibers 704, 708. In order to clear the passage ways through the hollow fibers 704, 708, the potting material 124 and the sealed ends of the fibers are trimmed away. A sharp knife or the like makes a slice generally coplanar with the central surface 1120. The exchanger after trimming is shown in FIGS. 1 and 2.

Referring to FIGS. 15 and 16, the manifolds 104, 120 are illustrated in perspective views. The venous or inlet manifold 104 can be the same as or different from the arterial or outlet manifold 120 in terms of geometry and resulting flow characteristics. In the event the venous manifold 104 and the arterial manifold 120 are the same, manufacturing costs can be reduced. Each manifold 104, 120 has an inlet end 1500 and outlet end 1504. The inlet end 1500 mates with a blood conduit such as a tube and the outlet end 1504 is connected to the case 108 by adhesive, welding or the like. The outlet end 1504 is coextensive with a wedge-shaped cavity 1512. Alignment tabs 1508 are provided on the manifolds to assure proper assembly during manufacture.

Figure 17:
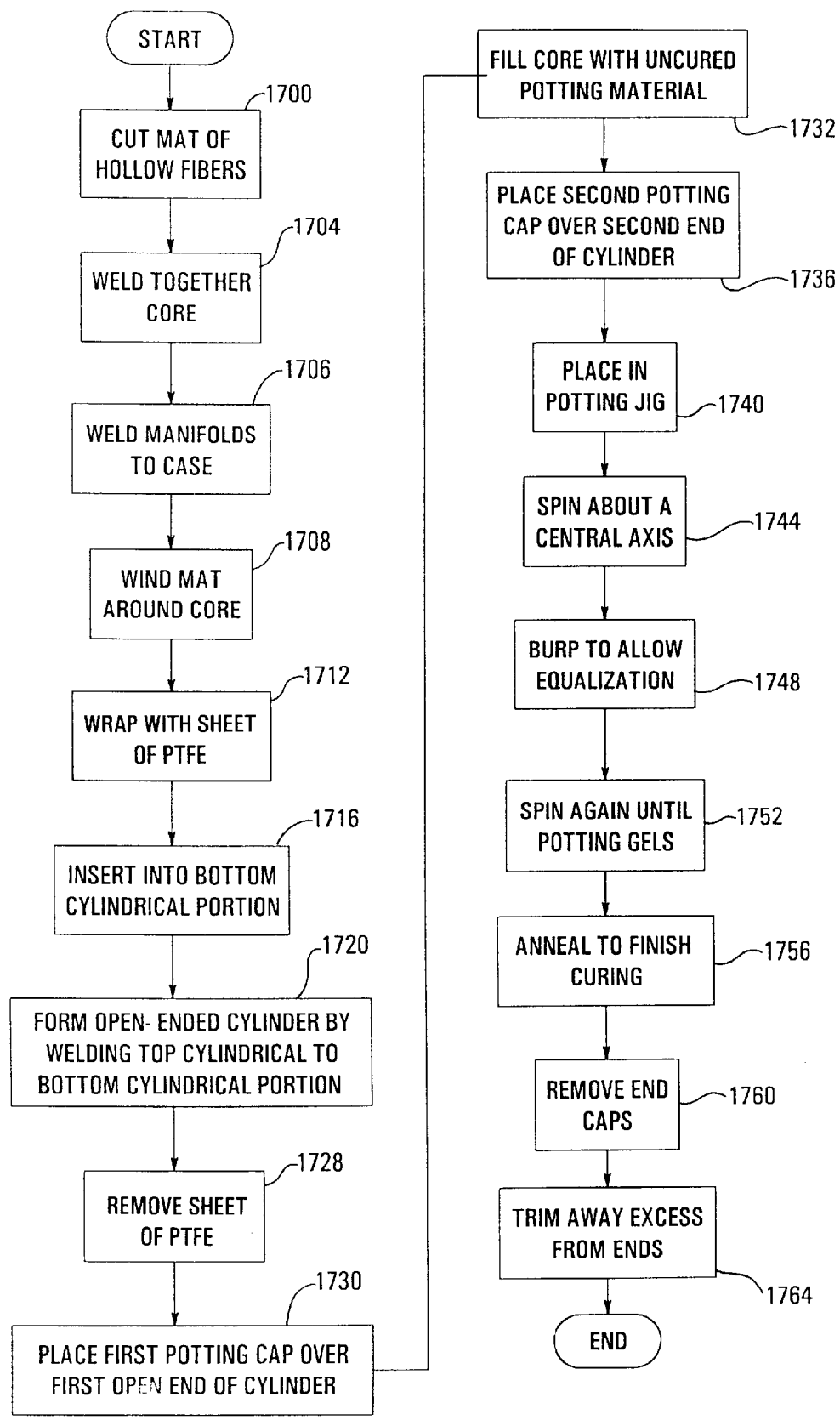
FIG. 17 is a flow diagram of an embodiment of the process of manufacturing an exchanger.

With reference to FIG. 17, a flow diagram of an embodiment of a method for manufacturing an exchanger is shown. This method achieves crimping the blood conduit 156, avoids external potting reservoirs and avoids delamination of the potting material 124. These problems are solved in an easy manufacturing process.

In the first step 1700, a mat of hollow fiber membranes 700 are cut. A hot blade or the like is used to perform the cut in order to both cut and seal the ends of the mat 700 in one step. The cut is generally parallel to the warp threads 712 such that the hollow fibers 704, 708 extend a length of the cut portion. The length of the cut is slightly larger than necessary in the finished exchanger. The extra length is trimmed away after potting in such a way as to open the sealed ends of the hollow fibers 704, 708. Once the sealed ends are removed, air can flow through the air conduit 160 unimpeded.

In step 1704, the core 116 is assembled. The core is comprised of the cylindrical portion 404 and the top portion 400. The top portion 400 is attached to the cylindrical portion 404 in such a way that the dispensing holes 412 on each end occupy the same plane. Either a weld, an adhesive or the like can be used to interconnect the top portion 400 to the cylindrical portion 404.

In step 1706, the manifolds 104, 120 are attached to top and bottom cylindrical portions 800, 804 which form the exchanger. The manifolds 104, 120 complete the blood conduit 156 and serve to disburse the narrow inlet of blood about substantially the whole length of the exchange chamber 164. In other embodiments however, the manifolds 104, 120 can be attached at other times provided that they are attached before step 1716 in which the core subassembly is inserted in the bottom cylindrical portion 804. Alternatively, the manifolds 104, 120 can be molded into the case 108 itself.

The hollow fiber bundle 112 is formed around the core in step 1708. The hollow fibers 704, 708 in the mat 700 are wound around the core 116 to form a core subassembly. Controlling the finished diameter of the core subassembly is desirable, however, the crimping allows for a less rigid tolerance on the diameter. If the core subassembly is too small, the case 108 may not adequately crimp the fiber bundle 112 such that shunting is avoided. The core subassembly can be somewhat larger than necessary without causing manufacturing problems because the case 108 is formed in two portions 800, 804. Accordingly, the diameter of the core subassembly does not require the tight tolerances of the conventional methods.

After steps 1712 and 1716, the case 108 is half assembled around the core subassembly. A thin sheet of Teflon™ is wrapped around the core subassembly in step 1712. Preferably, the Teflon™ sheet circumscribes more than half of the core subassembly, but less than the whole so that at least the regions of the core subassembly near the edges 920, 932 of the case 108 are covered with the sheet. The sheet protects the fiber bundle during assembly and welding of the case 108. The core subassembly wrapped in the sheet is inserted into the bottom cylindrical portion 804 in step 1716.

Assembly of the case 108 is completed in step 1720 and 1728. The open-ended cylindrical case 108 is formed in step 1720 by hot-plate welding the top and bottom cylindrical portions 800, 804 together, as described more fully above. Care is taken to avoid pinching the Teflon™ sheet during this process. As described above, the top cylindrical portion 800 has outwardly flared terminal portions 936 to help avoid pinching during this process. In step 1728, the Teflon™ sheet is pulled out from between the fiber bundle 112 and case 108.

Once the case construction is complete, the potting process may begin. Potting material 124 seals the exchange chamber 164 such that the blood conduit 156 is isolated from the air conduit 160 by the fiber membranes 704, 708. Before adding the potting material, one potting cap 1100 is placed on a first open end of the case which is away from the fill hole 408 in step 1730. If any potting material leaks from the core chamber 116 during the fill process, the potting cap 1100 will keep it from spilling on the ground. In step 1732, the core 116, which defines a chamber or reservoir, is partially filled with uncured potting material. The core 116 is filled quickly enough that significant amounts of potting material do not leak from the dispensing holes 412 before the subsequent potting steps are conducted. Moreover, the viscosity of the potting material largely resists leakage, and the potting cap 1100 serves to retain any leakage. Typically, the core 116 is filled with the dispensing holes 412 in a horizontal alignment. After filling, a core plug 1000 is used to cap the fill hole 408.

In steps 1736 and 1740, the exchanger is prepared for the potting process. The second open end of the case 108 near the fill hole 408 is enclosed with another potting cap 1100 in step 1736. The potting caps 1100 provide a mold for the uncured potting material so that, after curing, solid conjugates of the potting caps 1100 are formed. The exchanger enclosed with the end caps 1100, is placed in the potting jig 1300 in step 1740. The potting jig 1300 is used to hold the end caps 1100 in place during potting. As described above, counterweights 1316 rely upon centrifugal force to respectively bias the end caps 1100 toward the case 108 in order to create a seal. When the exchanger is placed in the jig 1300, the exchanger is typically oriented so that the dispensing holes 412 are in a horizontal plane.

In steps 1744, 1748 and 1752, the potting material is dispensed and partially cured in order to create the desired molded form. The potting jig and exchanger are attached to a centrifuge with an axis approximately half way between the ends of the case 108 and perpendicular to the length of the case 108. To allow the uncured potting material to flow from the core 116, the exchanger is rotated to align the dispensing holes 412 in a vertical plane. In step 1744, the exchanger is spun to create centrifugal force which dispenses the uncured potting material into the area of the potting caps 1100. In this way, potting material flows to each end simultaneously. The dispensing of the potting material can cause a low pressure area or vacuum to form in the core 116 in place of the potting material. To avoid formation of a vacuum that impedes the potting process, a high number of dispensing holes can be used. For example, if four dispensing holes in each end are used, it has been found that a vacuum that impedes the potting process is not formed. Alternatively, if a vacuum is formed, to equalize this pressure differential, as shown in step 1748, the spinning can be momentarily interrupted so that one of the dispensing holes serves as a conduit between the core and the area outside the core. In step 1752, spinning resumes and continues until the potting material is partially cured or "gelled" in the molded shape. This partial cure takes approximately 15 minutes and can be accelerated by applying heat. The catalyst for curing can be heat, evaporation, light, or any other known methods. In one embodiment, a urethane potting material has a catalyst mixed in where the quantity of the catalyst affects the cure time.

The potting process is completed in steps 1756 and 1760. Completion of the curing does not require centrifugal force since the potting material is set in the desired molded shape. In step 1756, the exchanger is annealed at approximately 55° C. for approximately 45 minutes to substantially complete the curing process. Before cooling, but after the potting material has gelled, the potting caps 1100 are removed in step 1760. Generally, the potting material 124 completely encloses the hollow fiber bundle 112.

In order to clear the air conduits 160, the excess potting material is trimmed away in step 1764. A sharp instrument is pressed against the potting material to slice it. Rocking or sawing aids in the slicing process. The location of the cut or slice is away from the case 108, and the annular relief 168 advantageously resists delamination. As can be appreciated, the pressure from the sharp instrument can cause deformation of the potting material, but its plasticity will allow it to regain its original shape after cutting. If the cut were adjacent to the case/potting material junction, delamination would be more likely to occur. According to the forgoing description, an improved exchanger is manufactured.

A number of variations and modifications of the invention can also be used. Although in the forgoing description the blood conduit is outside the hollow fibers and the air conduit is inside the hollow fibers, the air and blood could be reversed. In this way, the blood would flow through the hollow fibers, and the air would flow outside. Additionally, even though the exchanger was discussed in the context of an extra-corporeal blood oxygenator, the concepts are equally applicable to other types of membrane exchangers, such as reverse osmosis filters, membrane dialyzers, heat exchangers. Further, the shape of the disclosed exchanger is generally cylindrical, but, the teachings apply equally to rectangular or other shapes of exchangers. Further still, the trimming step could be performed by a laser cutting tool which would avoid direct contact which plastically deforms the potting material.

To simultaneously dispense the uncured potting material in the above embodiments, centrifugal force is used. Many exchangers could be stacked together to perform the centrifugal dispensing more efficiently. Additionally, gravity or other methods could be used to dispense the potting material from the integral potting reservoir. Further, it is not necessary to simultaneously disburse the potting material to both ends. The exchanger could have two separate chambers in the core. By successively spinning about one end, the potting material in each chamber could be serially disbursed.

Various other modifications and additions to the disclosed embodiment of the present invention may also be made without departing from the spirit and scope of the invention. However, it is to be expressly understood that such modifications and additions are within the scope of the present invention as set forth in the following claims.

What is claimed is:

1. An exchanger, comprising:
   a core having a length;
   a hollow fiber bundle having a plurality of hollow fibers extending around the core and along the length of the core; and
   a substantially cylindrical case positioned around the plurality of hollow fibers, the case having an inlet port at a first radial position and an outlet port at a second radial position, the cylindrical case having an interior surface adjacent the hollow fiber bundle, the interior surface having a reduced diameter portion between third and fourth radial positions spaced about 90 degrees from the first and second radial positions, the reduced diameter position being configured to crimp the hollow fiber bundle along the length of the core at the third and fourth radial positions.

2. The exchanger of claim 1, wherein the cylindrical case comprises first and second partial cylinders.

3. The exchanger of claim 2, wherein a first interior wall of the first partial cylinder has a first radius and at least a portion of a second interior wall of the second partial cylinder has a second radius different from the first radius.

4. The exchanger of claim 3, wherein the first and second partial cylinders are joined along edges running a length of the cylindrical case.

5. The exchanger of claim 4, wherein the first interior wall of the first partial cylinder edge has a third radius greater than the first and second radii.

6. The exchanger of claim 4, wherein the partial cylinder edges are coupled by hot plate welding.

7. The exchanger of claim 1, wherein the third radial position is substantially opposite the fourth radial position.

8. The exchanger of claim 7, wherein the first radial position is substantially opposite the second radial position and the first and second radial positions are about midway between the third and fourth radial positions.

9. The exchanger of claim 1, wherein the core further comprises a potting reservoir.

10. The exchanger of claim 1, wherein the plurality of hollow fibers includes a mat of hollow fibers rolled around the core.

11. The exchanger of claim 1, wherein the inlet and outlet ports and a space between the plurality of hollow fibers define a liquid conduit and wherein interiors of the plurality of hollow fibers define a gas conduit.

12. The exchanger of claim 1, wherein the plurality of hollow fibers are microporous and semi-permeable.

13. The exchanger of claim 1, wherein the plurality of hollow fibers are potted at ends of the core.

14. The exchanger of claim 1, wherein the exchanger is a blood oxygenator.

15. An exchanger, comprising:

a core having a length;

a hollow fiber bundle having a plurality of hollow fibers extending around the core and along the length of the core; and a substantially cylindrical case comprising first and second partial cylinders joined along edges running a length of the cylindrical case, a first interior wall of the first partial cylinder having a first radius and at least a portion of a second interior wall of the second partial cylinder having a second radius different from the first radius, the cylindrical case positioned around the plurality of hollow fibers and having an inlet port at a first radial position and an outlet port at a second radial position, the cylindrical case having an interior surface adjacent the hollow fiber bundle, the interior surface having a reduced diameter portion between third and fourth radial positions spaced about 90 degrees from the first and second radial positions, the reduced diameter position being configured to crimp the hollow fiber bundle along the length of the core at the third and fourth radial positions.

16. The exchanger of claim 15 wherein the first interior wall of the first partial cylinder has a third radius greater than the first and second radii.

17. The exchanger of claim 15 wherein the partial cylinder edges are coupled by hot plate welding.

18. A mass transfer device, comprising:

a core;

a plurality of hollow fibers arranged around the core;

an open ended cylinder which, at least partially, encases the core and the plurality of hollow fibers, the open ended cylinder having at least first and second partial cylinders, a first radius of the first partial cylinder being different from a second radius of the second partial cylinder;

an inlet manifold; and an outlet manifold, wherein the inlet and outlet manifolds are coextensive with substantially a whole length of the open ended cylinder.

19. A mass transfer device, comprising:

a core;

a plurality of hollow fibers arranged around the core;

an open ended cylinder which, at least partially, encases the core and the plurality of hollow fibers, the open ended cylinder having at least first and second partial cylinders, a first radius of the first partial cylinder being different from a second radius of the second partial cylinder, wherein the first partial cylinder has a first edge along one length, the second partial cylinder has a second edge along one length, the first edge flares outwardly from a substantially arcuate shape of a first interior wall of the first partial cylinder, the second edge flares outwardly from a substantially arcuate shape of a second interior wall of the second partial cylinder, and the first edge is coupled to the second edge.

\* \* \* \* \*